United States Patent
Minamoto et al.

(10) Patent No.: US 11,384,045 B2
(45) Date of Patent: Jul. 12, 2022

(54) METHOD FOR PRODUCING 1,3-BISACYLOXY-2-METHYLENE PROPANE

(71) Applicant: KURARAY CO., LTD., Okayama (JP)

(72) Inventors: Naoya Minamoto, Kamisu (JP); Yusuke Murata, Tsukuba (JP)

(73) Assignee: KURARAY CO., LTD., Okayama (JP)

( * ) Notice: Subject to any disclaimer, the term of this patent is extended or adjusted under 35 U.S.C. 154(b) by 0 days.

(21) Appl. No.: 17/261,967

(22) PCT Filed: Jul. 24, 2019

(86) PCT No.: PCT/JP2019/028950
§ 371 (c)(1),
(2) Date: Jan. 21, 2021

(87) PCT Pub. No.: WO2020/022364
PCT Pub. Date: Jan. 30, 2020

(65) Prior Publication Data
US 2021/0347721 A1 Nov. 11, 2021

(30) Foreign Application Priority Data
Jul. 27, 2018 (JP) .............................. JP2018-141805

(51) Int. Cl.
*C07C 67/297* (2006.01)
*C07C 67/055* (2006.01)

(52) U.S. Cl.
CPC .......... *C07C 67/297* (2013.01); *C07C 67/055* (2013.01)

(58) Field of Classification Search
None
See application file for complete search history.

(56) References Cited

U.S. PATENT DOCUMENTS

| | | | | |
|---|---|---|---|---|
| 3,872,163 A * | 3/1975 | Shimizu | ................. | C07C 69/16 560/244 |
| 3,970,713 A * | 7/1976 | Scharfe | ................. | C07C 67/055 568/877 |
| 4,480,123 A * | 10/1984 | Fischer | ................. | C07C 67/055 560/244 |
| 4,602,103 A | 7/1986 | Lyons | | |
| 5,777,155 A | 7/1998 | Sato et al. | | |
| 5,859,287 A * | 1/1999 | Nicolau | ................. | B01J 37/0201 560/241 |
| 2005/0234262 A1 * | 10/2005 | Inoue | ................. | B01J 23/52 560/241 |
| 2010/0076217 A1 * | 3/2010 | Yamamoto | ............. | B01J 23/683 560/231 |

FOREIGN PATENT DOCUMENTS

| | | | |
|---|---|---|---|
| DE | 1909964 | 9/1970 | |
| GB | 1138366 | * 1/1969 | ............. C07C 43/14 |
| JP | 47-28965 | 7/1972 | |
| JP | 52-27710 | 3/1977 | |
| JP | 53-127409 | 11/1978 | |
| JP | 2-264781 | 10/1990 | |
| JP | 8-3110 | 1/1996 | |
| JP | 2001-162163 | 6/2001 | |
| JP | 2004-256459 | 9/2004 | |
| JP | 2004256459 | * 9/2004 | ............. B01J 23/52 |
| JP | 2013-177576 | 9/2013 | |

OTHER PUBLICATIONS

Sanda et al., "Synthesis and Radical Polymerization of Spiroorthocarbonates Bearing exo-Methylene Groups", *Macromolecules*, vol. 26, No. 4, pp. 737-743 (1993).
International Search Report issued in PCT/JP2019/028950, dated Oct. 8, 2019, along with an English translation thereof.
Extended European Search Report issued in EP App. No. 19840196.0, dated Mar. 28, 2022.

* cited by examiner

*Primary Examiner* — Amy C Bonaparte
(74) *Attorney, Agent, or Firm* — Greenblum & Bernstein, P.L.C.

(57) ABSTRACT

A method for producing a 1,3-bisacyloxy-2-methylenepropane represented by the following general formula (II), including reacting a carboxylic acid represented by the following general formula (I), isobutylene, and oxygen, in a liquid phase, in the presence of a catalyst containing a carrier having carried thereon palladium and a transition metal of Group 11 in the periodic table, and a catalyst activator.

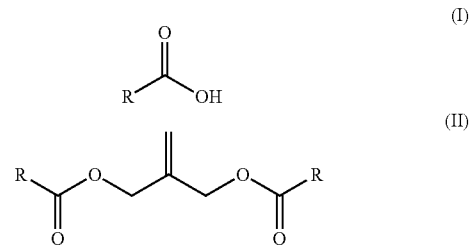

6 Claims, No Drawings

METHOD FOR PRODUCING 1,3-BISACYLOXY-2-METHYLENE PROPANE

TECHNICAL FIELD

The present invention relates to a method for producing a 1,3-bisacyloxy-2-methylenepropane.

BACKGROUND ART

A 1,3-bisacyloxy-2-methylenepropane has in one molecule thereof a 2,2-substituted carbon-carbon unsaturated bond applicable to radical addition reaction, hydrosilylation reaction, hydroformylation reaction, and the like, and two acyl groups applicable to saponification reaction, ester exchange reaction, and the like, and thereby can be used as a production raw material of various chemical products due to the reactivity thereof (see, for example, PTLs 1 and 2).

Some production methods of a 1,3-bisacyloxy-2-methylenepropane have been known.

For example, NPL 1 describes a method for producing 1,3-diacetoxy-2-methylenepropane through reaction of 1,3-dichloro-2-methylenepropane and sodium acetate.

However, the production method generates an inorganic by-product, which generally becomes a waste material, in the equimolar amount or more with respect to the product. Accordingly, a production method that does not generate an inorganic by-product is demanded from the standpoint of the reduction of environmental load.

As a production method that does not generate an inorganic by-product, a method for producing a 1,3-bisacyloxy-2-methylenepropane through reaction of a terminal olefin compound, a carboxylic acid, and oxygen in a gas phase in the presence of a solid catalyst has been known.

For example, PTL 3 describes a method for producing 1,3-diacetoxy-2-methylenepropane through reaction of methallyl acetate, acetic acid, water, and oxygen in a gas phase in the presence of the particular catalyst. PTL 3 describes that a mixed gas of nitrogen/oxygen/methallyl acetate/acetic acid/water=40.0/2.0/1.2/5.0/3.0 (mol/hr) is fed to 900 mL of the solid catalyst at 2 atm to perform gas phase reaction at a reaction temperature of 140° C., and thereby 1,3-diacetoxy-2-methylenepropane is obtained with a conversion of methallyl acetate of 25% and a selectivity of 95% (the production efficiency of 1,3-diacetoxy-2-methylenepropane is 55 g/(L(catalyst)·hr).

PTL 4 describes a method for producing 1,3-diacetoxy-2-methylenepropane through reaction by feeding a mixed gas containing isobutylene, acetic acid, and oxygen to a palladium catalyst in a gas phase, and describes that methallyl acetate by-produced is recycled and added to the reaction gas. PTL 4 describes that a mixed gas of acetic acid/oxygen/isobutylene/methallyl acetate/steam=20/10/50/10/10 is fed at a rate of 4 L per hour to 10 mL of the solid catalyst to perform gas phase reaction at a reaction temperature of 155° C., and thereby 1,3-diacetoxy-2-methylenepropane is obtained with a production efficiency of 67 g/(L (catalyst)·hr).

A method for producing an unsaturated ester through reaction of a terminal olefin compound, a carboxylic acid, and oxygen in a liquid phase in the presence of a solid catalyst has been known.

For example, PTL 5 describes a method for producing methallyl acetate through reaction of isobutylene, acetic acid, and oxygen in the presence of a solid catalyst having an element composition shown by XaYb (wherein X represents at least one of Pd, Pt, and Rh, Y represents at least one of Bi, Sb, S, Te, V, and Nb, and 0<b<20 assuming a=1). PTL 5 describes that 10.0 g of acetic acid, 1.00 g of a hydrocarbon mixture containing 30% of isobutylene, and oxygen gas are subjected to liquid phase reaction at a reaction temperature of 85° C. in the presence of 1.00 g of the particular solid catalyst, and thereby methallyl acetate is obtained with a selectivity of 92% and a conversion of isobutylene of 71%, but there is no description about the production of a 1,3-bisacyloxy-2-methylenepropane.

CITATION LIST

Patent Literatures

PTL 1: JP 2013-177576 A
PTL 2: JP 2-264781 A
PTL 3: German Patent No. 1,909,964
PTL 4: JP 47-28965 B
PTL 5: JP 53-127409 A

Non-Patent Literature

NPL 1: Macromolecules, 1993, 26(4), pp. 737-743

SUMMARY OF INVENTION

Technical Problem

All the ordinary methods for producing a 1,3-bisacyloxy-2-methylenepropane that do not generate an inorganic by-product use reaction under the gas phase condition. In the reaction under the gas phase condition, the oxygen concentration is necessarily the critical oxygen concentration or lower from the standpoint of safety, which constrains an operation with a low substrate conversion, requiring a recovery device for the substrate. Furthermore, the reaction requires a vaporizer of the raw materials, a reaction tube filled with the catalyst, and an enormous amount of energy for vaporizing the raw materials, and therefore there is large room for improvement in all the standpoints of the production efficiency, the equipment cost, and the energy consumption.

In view of the circumstances, a problem to be solved by the present invention is to provide a method for producing a 1,3-bisacyloxy-2-methylenepropane that does not generate an inorganic by-product in the equimolar amount or more with respect to the product and is improved in production efficiency and cost.

Solution to Problem

As a result of the earnest investigations for solving the problem, the present inventors have found that the problem can be solved by employing a particular liquid phase condition in the production of a 1,3-bisacyloxy-2-methylenepropane through oxidative reaction of isobutylene and a carboxylic acid, and the present invention has been completed by performing further investigations based on the knowledge.

Specifically, the present invention is as follows.

[1] A method for producing a 1,3-bisacyloxy-2-methylenepropane represented by the following general formula (II), including reacting a carboxylic acid represented by the following general formula (I), isobutylene, and oxygen, in a liquid phase, in the presence of a catalyst containing a carrier having carried thereon palladium and a transition metal of Group 11 in the periodic table, and a catalyst activator:

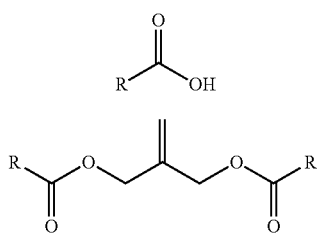

wherein R represents a hydrogen atom, an alkyl group having 1 to 8 carbon atoms, which may have a substituent, a cycloalkyl group having 3 to 8 carbon atoms, which may have a substituent, an alkenyl group having 2 to 6 carbon atoms, which may have a substituent, or an aryl group having 6 to 14 carbon atoms, which may have a substituent.

[2] The production method according to the item [1], wherein an amount of the carboxylic acid used is more than 1 mol and 50 mol or less per 1 mol of the isobutylene.

[3] The production method according to the item [1] or [2], wherein the carboxylic acid is acetic acid, and the 1,3-bisacyloxy-2-methylenepropane is 1,3-diacetoxy-2-methylenepropane.

[4] The production method according to any one of the items [1] to [3], wherein an amount of the catalyst used is from 0.01 to 20% by mass based on the total mass of the carboxylic acid and the isobutylene.

[5] The production method according to any one of the items [1] to [4], wherein the catalyst activator is at least one kind selected from a hydroxide, a nitrate salt, a carboxylate salt, and a carbonate salt of an alkali metal or an alkaline earth metal.

[6] The production method according to any one of the items [1] to [5], wherein an amount of the catalyst activator used is from 1 to 20% by mass based on the total amount of the mass of the carrier and the amount of the catalyst activator used as 100% by mass.

[7] The production method according to any one of the items [1] to [6], wherein a reaction temperature in the reaction in a liquid phase is from 80 to 200° C.

Advantageous Effects of Invention

According to the present invention, a method for producing a 1,3-bisacyloxy-2-methylenepropane that does not generate an inorganic by-product in the equimolar amount or more with respect to the product and is improved in production efficiency and cost can be provided.

DESCRIPTION OF EMBODIMENTS

The present invention will be described in detail below.

While preferred embodiments of the present invention will be described along with the matters defining the present invention, an embodiment combining two or more of the individual preferred embodiments is also a preferred embodiment of the present invention. In the case where there are plural numeral ranges for the matter shown by a numeral range, a combination of the lower limit and the upper limit that are selected from the plural ranges may also be a preferred embodiment.

The method for producing the 1,3-bisacyloxy-2-methylenepropane represented by the general formula (II) (which may be hereinafter abbreviated as a "1,3-bisacyloxy-2-methylenepropane (II)") of the present invention includes reacting the carboxylic acid represented by the general formula (I) (which may be hereinafter abbreviated as a "carboxylic acid (I)"), isobutylene, and oxygen, in the presence of a catalyst containing a carrier having carried thereon palladium and a transition metal of Group 11 in the periodic table, and a catalyst activator, in a liquid phase.

In the reaction, formally, one equivalent of isobutylene and two equivalents of the carboxylic acid (I) undergo oxidative dehydration condensation, so as to form the 1,3-bisacyloxy-2-methylenepropane (II) and water.

The reaction formula in a preferred embodiment of the present invention is as follows.

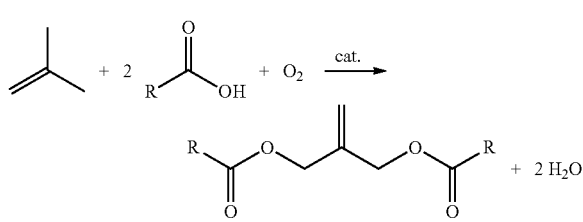

In the formula, R has the same meaning as R in the general formulae (I) and (II).

In the production method of the present invention, the costs of energy and equipment can be suppressed by employing the reaction under a liquid phase condition.

As a result of the investigations by the present inventors, it has been found that in a gas phase condition, the 1,3-bisacyloxy-2-methylenepropane (II) as the product is adsorbed on the catalyst and inhibits the reaction, and the deactivation of the catalyst occurs at a high temperature for retaining the gaseous state of the product, due to the high boiling point thereof. Accordingly, it is difficult to enhance the productivity in a gas phase condition, and a liquid phase condition is advantageous from the standpoint of the production efficiency.

(Raw Materials and Target Product)

In the general formula (I) representing the carboxylic acid as the raw material and the general formula (II) representing the 1,3-bisacyloxy-2-methylenepropane as the target product, R represents a hydrogen atom, an alkyl group having 1 to 8 carbon atoms, which may have a substituent, a cycloalkyl group having 3 to 8 carbon atoms, which may have a substituent, an alkenyl group having 2 to 6 carbon atoms, which may have a substituent, or an aryl group having 6 to 14 carbon atoms, which may have a substituent.

The alkyl group having 1 to 8 carbon atoms represented by R may be linear or branched, and examples thereof include a methyl group, an ethyl group, a n-propyl group, an isopropyl group, a n-butyl group, a sec-butyl group, an isobutyl group, a tert-butyl group, a n-pentyl group, a n-hexyl group, and a n-octyl group.

In the alkyl group having 1 to 8 carbon atoms represented by R, one or more hydrogen atom may be substituted by a substituent. Examples of the substituent include a cycloalkyl group having 3 to 8 carbon atoms, an aryl group having 6 to 14 carbon atoms, an alkoxy group having 1 to 8 carbon atoms, an aryloxy group having 6 to 14 carbon atoms, and a silyl group. In the case where the alkyl group having 1 to 8 carbon atoms represented by R has a substituent, the number of the substituent is preferably 1 to 3. In the case where the alkyl group having 1 to 8 carbon atoms represented by R has plural substituents, the substituents may be the same as or different from each other.

Examples of the cycloalkyl group having 3 to 8 carbon atoms as the substituent include the same ones as exemplified for the cycloalkyl group having 3 to 8 carbon atoms represented by R described later.

Examples of the aryl group having 6 to 14 carbon atoms as the substituent include the same ones as exemplified for the aryl group having 6 to 14 carbon atoms represented by R described later.

Examples of the alkoxy group having 1 to 8 carbon atoms as the substituent include linear, branched, and cyclic alkoxy groups, such as a methoxy group, an ethoxy group, a propoxy group, a t-butoxy group, a pentyloxy group, a cyclopentyloxy group, a hexyloxy group, a cyclohexyloxy group, a 2-ethylhexyloxy group, and an octyloxy group.

Examples of the aryloxy group having 6 to 14 carbon atoms as the substituent include a phenoxy group and a naphthoxy group.

Examples of the silyl group as the substituent include a trimethylsilyl group, a triethylsilyl group, a t-butyldimethylsilyl group, a t-butyldiphenylsilyl group, and a triphenylsilyl group.

The cycloalkyl group having 3 to 8 carbon atoms represented by R may be any of monocyclic, polycyclic, and condensed ring, and examples thereof include a cyclopropyl group, a cyclopentyl group, and a cyclohexyl group.

In the cycloalkyl group having 3 to 8 carbon atoms represented by R, one or more hydrogen atom may be substituted by a substituent. Examples of the substituent include an alkyl group having 1 to 8 carbon atoms that is the same as the examples of the alkyl group having 1 to 8 carbon atoms represented by R described above, a cycloalkyl group having 3 to 8 carbon atoms that is the same as the examples of the cycloalkyl group having 3 to 8 carbon atoms represented by R described above, and an aryl group having 6 to 14 carbon atoms, an alkoxy group having 1 to 8 carbon atoms, an aryloxy group having 6 to 14 carbon atoms, and a silyl group that are the same as the examples of the substituent described above. In the case where the cycloalkyl group having 3 to 8 carbon atoms represented by R has a substituent, the number of the substituent is preferably 1 to 3. In the case where the cycloalkyl group having 3 to 8 carbon atoms represented by R has plural substituents, the substituents may be the same as or different from each other.

Examples of the alkenyl group having 2 to 6 carbon atoms represented by R include an ethenyl group (vinyl group), a 1-methylethenyl group, a 1-propenyl group, a 2-propenyl group (allyl group), a 1-methyl-1-propenyl group, a 1-methyl-2-propenyl group, a 1-butenyl group, a 2-butenyl group, and a 3-butenyl group.

In the alkenyl group having 2 to 6 carbon atoms represented by R, one or more hydrogen atom may be substituted by a substituent. Examples of the substituent include the same ones as exemplified for the substituent that may be had in the case where R represents an alkyl group having 1 to 8 carbon atoms. In the case where the alkenyl group having 2 to 6 carbon atoms represented by R has a substituent, the number of the substituent is preferably 1 to 3. In the case where the alkenyl group having 2 to 6 carbon atoms represented by R has plural substituents, the substituents may be the same as or different from each other.

The aryl group having 6 to 14 carbon atoms represented by R may be any of monocyclic, polycyclic, and condensed ring, and examples thereof include a phenyl group, a naphthyl group, an anthryl group, and a phenanthryl group.

In the aryl group having 6 to 14 carbon atoms represented by R, one or more hydrogen atom may be substituted by a substituent. Examples of the substituent include the same ones as exemplified for the substituent that may be had in the case where R represents a cycloalkyl group having 3 to 8 carbon atoms. In the case where the aryl group having 6 to 14 carbon atoms represented by R has a substituent, the number of the substituent is preferably 1 to 3. In the case where the aryl group having 6 to 14 carbon atoms represented by R has plural substituents, the substituents may be the same as or different from each other.

From the standpoint of the availability, R preferably represents an alkyl group having 1 to 8 carbon atoms or an alkenyl group having 2 to 6 carbon atoms, more preferably one selected from the group consisting of a methyl group, an ethyl group, a n-propyl group, a 2-propyl group, a n-butyl group, 2-butyl group, an isobutyl group, an ethenyl group, and a 1-methylethenyl group, further preferably a methyl group or a 1-methylethenyl group, and most preferably a methyl group. Accordingly, the carboxylic acid (I) is most preferably acetic acid, and the 1,3-bisacyloxy-2-methylenepropane (II) is most preferably 1,3-diacetoxy-2-methylenepropane.

(Catalyst)

The catalyst used in the production method of the present invention is a catalyst containing a carrier having carried thereon palladium and a transition metal of Group 11 in the periodic table. The catalyst may be a commercially available product and may be synthesized by a known method.

Carrier

The carrier used may be, for example, a porous substance. Examples of the carrier include an inorganic carrier, such as silica, alumina, silica-alumina, diatom earth, montmorillonite, zeolite, titania, zirconia, and activated carbon; and a polymer compound, such as polystyrene, polyethylene, polyamide, and cellulose. These may be used alone or as a combination of two or more kinds thereof. Among these, an inorganic carrier is preferred, silica or alumina is more preferred, and silica is further preferred. Silica may contain impurities other than $SiO_2$.

The form of the carrier is not particularly limited, and may be appropriately selected depending on the reaction mode. Specific examples of the form thereof include a powder form, a spherical form, and a pellet form, and a spherical form is preferred. In the case where the carrier has a spherical form, the particle diameter is not particularly limited, and is preferably 1 to 10 mm. In the case where the particle diameter is 10 mm or less, the raw materials can readily penetrate sufficiently into the interior of the catalyst, and the reaction can readily proceed effectively. In the case where the particle diameter is 1 mm or more, the carrier can readily exhibit the function thereof sufficiently Palladium The catalyst used contains the carrier having palladium carried thereon. Palladium herein may be in the form of metallic palladium or a palladium compound. The palladium compound is not particularly limited, and examples thereof include palladium chloride, palladium acetate, palladium nitrate, palladium sulfate, sodium chloropalladate, potassium chloropalladate, and barium chloropalladate.

Transition Metal of Group 11 in Periodic Table

The carrier further has a transition metal of Group 11 in the periodic table, such as copper and gold, carried thereon, in addition to palladium described above. The transition metals may be used alone or as a combination of two or more kinds thereof. Among these, copper and gold are preferred, and gold is more preferred, from the standpoint of the enhancement of the production efficiency. The use form of the transition metal of Group 11 in the periodic table in the preparation of the catalyst is not particularly limited, and examples of the form include compound forms, such as a nitrate salt, a carbonate salt, a sulfate salt, an organic acid salt, and a halide.

The ratio of palladium and the transition metal of Group 11 in the periodic table is preferably 0.001 to 10 parts by mass, and more preferably 0.05 to 5 parts by mass, of the transition metal of Group 11 in the periodic table per 1 part by mass of palladium.

The preparation method of the catalyst containing a carrier having palladium and a transition metal of Group 11 in the periodic table carried thereon is not particularly limited, and for example, the catalyst may be obtained by performing sequentially the following steps (1) to (4).

Step (1)
Step of impregnating a carrier with an aqueous solution of a palladium salt and a compound containing a transition metal of Group 11 in the periodic table, so as to provide a catalyst precursor A Step (2)
Step of bringing the catalyst precursor A obtained in the step (1) without drying, into contact with an aqueous solution of an alkali metal salt, so as to provide a catalyst precursor B Step (3)
Step of bringing the catalyst precursor B obtained in the step (2), into contact with a reducing agent, such as hydrazine or formalin, so as to provide a catalyst precursor C Step (4)
Step of rinsing with water and drying the catalyst precursor C obtained in the step (3)

The catalyst obtained by the aforementioned preparation method preferably has a specific surface area of 10 to 250 $m^2/g$ and a pore volume of 0.1 to 1.5 mL/g.

The ratio of palladium and the carrier in the catalyst is preferably 10 to 1,000 parts by mass, and more preferably 30 to 500 parts by mass, of the carrier per 1 part by mass of palladium. In the case where the amount of the carrier is 10 parts by mass or more per 1 part by mass of palladium, the dispersion state of palladium can be enhanced to improve the reaction result. In the case where the amount of the carrier is 1,000 parts by mass or less per 1 part by mass of palladium, the industrial practicality can be enhanced.

The amount of the catalyst used in the production method of the present invention is not particularly limited, and is preferably 0.01 to 20% by mass, more preferably 0.1 to 10% by mass, further preferably 0.5 to 8% by mass, and still further preferably 1.0 to 5% by mass, based on the total mass of the carboxylic acid (I) and isobutylene, from the standpoint of the enhancement of the production efficiency.

(Catalyst Activator)
The catalyst activator used in the production method of the present invention may be used in the form carried on the catalyst in advance, or may be charged in the reaction device along with the reaction mixture. Examples of the catalyst activator include a hydroxide, a nitrate salt, a carboxylate salt, or a carbonate salt of an alkali metal, such as sodium, potassium, and cesium; and a hydroxide, a nitrate salt, a carboxylate salt, or a carbonate salt of an alkaline earth metal, such as magnesium, calcium, and barium. These catalyst activators may be used alone or as a combination of two or more kinds thereof. Among these, a salt of the carboxylic acid (I) is preferred, an alkali metal salt of the carboxylic acid (I) is more preferred, and potassium acetate is further preferred, from the standpoint of the availability and the reaction activity.

The amount of the catalyst activator used is not particularly limited, and is preferably 1 to 20% by mass, and more preferably 3 to 15% by mass, based on the total amount of the mass of the carrier and the amount of the catalyst activator used as 100% by mass.

(Oxygen)
Oxygen used in the production method of the present invention may be atomic and/or molecular oxygen, and is preferably molecular oxygen. In the case where molecular oxygen is used, a mixed gas with an inert gas, such as nitrogen, argon, helium, and carbon dioxide, is preferably used. In this case, it is more preferred that the oxygen concentration is controlled to such a range that the gas inside the system does not have an explosive composition.

Examples of the method of supplying molecular oxygen or a mixed gas containing molecular oxygen to the reaction system include a method of supplying to the liquid phase portion in the reaction system, a method of supplying to the gas phase portion therein, and a method of supplying to both the liquid phase portion and the gas phase portion.

Molecular oxygen or a mixed gas containing molecular oxygen is preferably supplied to the reaction system at an oxygen partial pressure in a range of 0.01 to 200 atm (gauge pressure), and more preferably 0.1 to 100 atm (gauge pressure).

(Solvent)
The reaction of the carboxylic acid (I), isobutylene, and oxygen in the presence of the catalyst and the catalyst activator in a liquid phase in the production method of the present invention may be performed by using a solvent or without a solvent.

Examples of the solvent that is used depending on necessity in the production method of the present invention include a hydrocarbon (including an aliphatic hydrocarbon and an aromatic hydrocarbon), such as hexane, heptane, methylcyclohexane, and benzene; a heterocyclic compound, such as pyridine and quinoline; an ether, such as diethyl ether, tetrahydrofuran, methyl tert-butyl ether, and cyclopentyl methyl ether; a ketone, such as acetone, methyl ethyl ketone, and isobutyl methyl ketone; an ester, such as a carboxylate ester, diethyl carbonate, and propylene carbonate; an amide, such as dimethylformamide and dimethylacetamide; a nitrile, such as acetonitrile and benzonitrile; and an alcohol, such as methanol, ethanol, isopropyl alcohol, and phenol. These may be used alone or as a combination of two or more kinds thereof.

In the case where a solvent is used in the reaction, the amount of the solvent used is not particularly limited, as far as the reaction is not adversely affected, and is generally approximately 0.1 to 1,000 times amount, and is preferably 0.4 to 100 times amount from the standpoint of the productivity, all based on the total mass of the carboxylic acid (I) and isobutylene.

(Reaction Condition)
In the production method of the present invention, the amount of the carboxylic acid (I) used is preferably more than 1 mol and 50 mol or less per 1 mol of the isobutylene. The amount of the carboxylic acid (I) used (i.e., the amount thereof used per 1 mol of the isobutylene) is preferably 2 mol or more, and more preferably 2.5 mol or more, and may be 5 mol or more, 10 mol or more, or 20 mol or more. The amount of the carboxylic acid (I) used is preferably 45 mol or less, more preferably 40 mol or less, and further preferably 35 mol or less. In the case where the amount thereof used is 1 mol or more, a further excellent production efficiency can be obtained. In the case where the amount thereof used is 50 mol or less, the process for recovering the excessive carboxylic acid (I) can be shortened, which is economically advantageous.

In the case where the carboxylic acid (I) is placed in the reaction system by dividing into multiple times, the amount thereof used is the total amount thereof placed.

The reaction conditions, such as the reaction temperature, the reaction pressure, and the reaction time, in the production method of the present invention may be appropriately determined depending on the kinds and the combination of the carboxylic acid (I), isobutylene, and the solvent used depending on necessity, the composition of the catalyst, and the like, and are not particularly limited.

For example, the reaction temperature is preferably in a range of 80 to 200° C. In the case where the reaction temperature is 80° C. or more, the 1,3-bisacyloxy-2-methylenepropane (II) can be efficiently produced without excessive decrease of the reaction rate. The reaction temperature is more preferably 90° C. or more, and further preferably 120° C. of more. In the case where the reaction temperature is 200° C. or less, side reaction including combustion can be prevented from occurring, and thereby the 1,3-bisacyloxy-2-methylenepropane (II) can be efficiently produced, and the corrosion of the reaction device due to the carboxylic acid can be suppressed. The reaction temperature is more preferably 180° C. or less, and further preferably 160° C. or less.

The reaction time may be in a range, for example, of 0.5 to 12 hours. The reaction time may be 1 hour or more from the standpoint of the production efficiency, and may be 10 hours or less or 8 hours or less from the same standpoint.

The reaction mode in the production method of the present invention may be either a continuous system or a batch system, and is not particularly limited. In the case where a batch system is used as the reaction mode, for example, the catalyst may be charged in the reaction device at one time along with the raw materials, and in the case where a continuous system is used as the reaction mode, for example, the catalyst may be charged in the reaction device in advance, or may be continuously charged in the reaction device along with the raw materials. The catalyst may be used in the form of any of a fixed bed, a fluidized bed, and a suspension bed.

(Purification)

In the production method of the present invention, purification may be performed after the aforementioned reaction. Specifically, the 1,3-bisacyloxy-2-methylenepropane (II) formed through the aforementioned reaction can be isolated by separating the catalyst and then purifying the reaction solution.

The measure for separating the catalyst is not particularly limited and may be an ordinary solid-liquid separation measure, and examples thereof used include filtration methods, such as natural filtration, pressure filtration, filtration under reduced pressure, and centrifugal filtration.

The measure for purifying the reaction solution is not particularly limited and may be a distillation method, an extraction method, column chromatography, or the like. These methods may be performed in combination. Among these, a distillation method and an extraction method are preferred.

The raw materials and the solvent separated by the purification may be used again for the reaction. The catalyst separated may also be used again in the reaction.

The production method of the present invention exemplified by the aforementioned embodiments can produce the 1,3-bisacyloxy-2-methylenepropane (II) as the target product with a high conversion, a high selectivity, and a high yield, without the formation of the inorganic by-product in the equimolar amount or more with respect to the target product.

EXAMPLES

The present invention will be described more specifically with reference to an example and comparative examples below, but the present invention is not limited thereto.

[Analysis Condition]

The solution after the reaction (reaction mixture) was analyzed by using a gas chromatograph GC2014 (produced by Shimadzu Corporation, FID detector) and a capillary column (produced by Agilent Technologies, Inc., DB-1, length: 30 m, inner diameter: 0.25 mm, thickness: 0.25 μm) under the following condition.

Column temperature: 50° C. (5 min)→10° C./min→250° C. (5 min)
FID temperature: 250° C.
Injection port temperature: 250° C.
Carrier gas: helium
Makeup gas: helium
Injection amount: 0.2 μL
Gas flow rate in column: 0.38 mL/min
Split ratio: 20

Production Example 1: Preparation of Catalyst 1

250 mL (144 g) of a silica carrier (5 mm in diameter) was immersed in an aqueous solution containing 4.00 g (13.6 mmol) of sodium tetrachloropalladate and 3.90 g (9.5 mmol) of tetrachloroauric acid tetrahydrate, and the entire amount of the aqueous solution was absorbed thereby. Subsequently, 200 mL of an aqueous solution containing 16 g (131 mmol) of sodium metasilicate was added thereto, and the mixture was allowed to stand for 20 hours. Thereafter, 9.50 g (190 mmol) of hydrazine monohydrate was added to reduce the palladium salt and the gold salt to metals. The catalyst after the reduction was rinsed with water and dried at 110° C. for 4 hours. Thereafter, the carrier having metallic palladium was placed in an aqueous solution containing 13.34 g (136 mmol) of potassium acetate, the entire amount of the aqueous solution was absorbed thereby, and then dried at 110° C. for 4 hours to prepare the catalyst 1.

Production Example 2: Preparation of Catalyst 2

250 mL (144 g) of a silica carrier (5 mm in diameter) was immersed in an aqueous solution containing 4.00 g (13.6 mmol) of sodium tetrachloropalladate and 3.90 g (9.5 mmol) of tetrachloroauric acid tetrahydrate, and the entire amount of the aqueous solution was absorbed thereby. Subsequently, 200 mL of an aqueous solution containing 16 g (131 mmol) of sodium metasilicate was added thereto, and the mixture was allowed to stand for 20 hours. Thereafter, 9.50 g (190 mmol) of hydrazine monohydrate was added to reduce the palladium salt and the gold salt to metals. The catalyst after the reduction was rinsed with water and dried at 110° C. for 4 hours to prepare the catalyst 2.

Example 1

1.3 g of the catalyst 1 obtained in Production Example 1, 47.7 g (794 mmol) of acetic acid, and 1.4 g (24 mmol) of isobutylene were charged in an electromagnetic stirring autoclave having a capacity of 100 mL equipped with a gas inlet port and a sampling port, a mixed gas of oxygen/nitrogen=8/92 (molar ratio) was introduced to the liquid phase to make the pressure inside the autoclave of 20 atm (gauge pressure), and then the temperature in the autoclave was increased to 140° C. under stirring. Thereafter, the reaction was performed for 5 hours while flowing a mixed gas of oxygen/nitrogen=8/92 (molar ratio) at a flow rate of 200 mL/min and retaining 90 atm (gauge pressure) with the mixed gas, so as to provide a reaction solution.

The analysis of the resulting reaction solution by the aforementioned method revealed that the conversion of isobutylene was 100%, and the selectivity to 1,3-diacetoxy-2-methylenepropane was 83%. The yield of 1,3-diacetoxy-2-methylenepropane obtained was 3.5 g (20 mmol), and the production efficiency of 1,3-diacetoxy-2-methylenepropane was 0.55 g(product)/(g(catalyst)·hr).

Comparative Example 1

The reaction was performed by performing the same procedure as in Example 1 except that the catalyst 2 was used instead of the catalyst 1, and the reaction was performed for 6 hours.

The analysis of the resulting reaction solution by the aforementioned method revealed that the conversion of isobutylene was 66%, the selectivity to 1,3-diacetoxy-2-methylenepropane was 10%, and the selectivity to methallyl acetate was 85%. The yield of 1,3-diacetoxy-2-methylenepropane obtained was 0.3 g (1.6 mmol), and the production efficiency of 1, 3-diacetoxy-2-methylenepropane was 0.037 g(product)/(g(catalyst)·hr).

Comparative Example 2

8.6 g (approximately 15 mL) of the catalyst 1 obtained in Production Example 1 was packed in a reaction tube formed of stainless steel having an inner diameter of 23 mm and a length of 20 cm, through which isobutylene, acetic acid, oxygen, nitrogen, and water were loaded at a volume ratio (in terms of gas) of isobutylene/acetic acid/oxygen/nitrogen/water=30/7/8/53/2 and a rate of 70.5 NL/hr, and reacted under pressure of 0.5 MPaG at 160° C. After 4 hours, the analysis of the composition in the outlet port of the reaction tube revealed that the production rates of 1,3-diacetoxy-2-methylenepropane and methallyl acetate were 0.16 g(product)/(g(catalyst)·hr) and 0.22 g(product)/(g(catalyst)·hr) respectively, and the yields of 1,3-diacetoxy-2-methylenepropane and methallyl acetate with respect to isobutylene loaded to the reaction tube were 0.8% and 1.8% respectively. Carbon dioxide was generated at a selectivity of 6.9% with respect to isobutylene reacted.

Thereafter, after loading only nitrogen at 160° C. under the atmospheric pressure at a rate of 70 NL/hr for 1 hour, the reaction tube was cooled to room temperature, and the catalyst was taken out therefrom. 1 g of the catalyst was immersed in 10 mL of methanol, and the analysis of the solution confirmed the presence of 1,3-diacetoxy-2-methylenepropane. Accordingly, it was found that 1,3-diacetoxy-2-methylenepropane was not sufficiently vaporized but was adsorbed on the catalyst under the reaction condition.

The results of Example 1 and Comparative Examples 1 and 2 shown above are shown in Table 1.

TABLE 1

| | Reaction phase | Catalyst | Reaction time | Conversion *3 | Selectivity *1 | Yield *3 | Production efficiency *2 |
|---|---|---|---|---|---|---|---|
| Example 1 | liquid phase | catalyst 1 | 5 hours | 100% | 83% | 83% | 0.55 |
| Comparative Example 1 | liquid phase | catalyst 2 | 6 hours | 66% | 10% | 7% | 0.037 |
| Comparative Example 2 | gas phase | catalyst 1 | 4 hours | — | — | 0.8% | 0.16 |

The expressions in Table 1 are as follows.
*1 Selectivity to 1,3-bisacyloxy-2-methylenepropane (II) in product
*2 Production efficiency of 1,3-bisacyloxy-2-methylenepropane (II) (g(product)/(g(catalyst) ·0 hr))
*3 Based on isobutylene Example 1 shows an excellent selectivity, from which it is understood that an inorganic by-product is not formed in the equimolar amount or more with respect to the product. It is also understood from the conversion, the selectivity, and the yield that Examples are excellent in production efficiency as compared to Comparative Examples.

INDUSTRIAL APPLICABILITY

According to the production method of the present invention, a 1,3-bisacyloxy-2-methylenepropane can be produced without the generation of an inorganic by-product in the equimolar amount or more with high production efficiency and cost efficiency. A 1,3-bisacyloxy-2-methylenepropane can be used as a production raw material of various industrially useful compounds.

The invention claimed is:

1. A method for producing a 1,3-bisacyloxy-2-methylenepropane represented by the following general formula (II), comprising reacting a carboxylic acid represented by the following general formula (I), isobutylene, and oxygen, in a liquid phase, in the presence of a catalyst containing a carrier having carried thereon palladium and a transition metal of Group 11 in the periodic table, and a catalyst activator:

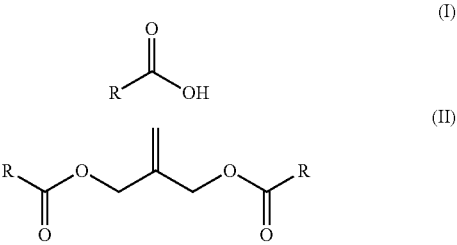

wherein R represents a hydrogen atom, an alkyl group having 1 to 8 carbon atoms, which may have a substituent, a cycloalkyl group having 3 to 8 carbon atoms, which may have a substituent, an alkenyl group having 2 to 6 carbon atoms, which may have a substituent, or an aryl group having 6 to 14 carbon atoms, which may have a substituent, and wherein the catalyst activator is at least one kind selected from a hydroxide, a nitrate salt, a carboxylate salt, and a carbonate salt of an alkali metal or an alkaline earth metal.

2. The production method according to claim 1, wherein an amount of the carboxylic acid used is more than 1 mol and 50 mol or less per 1 mol of the isobutylene.

3. The production method according to claim 1, wherein the carboxylic acid is acetic acid, and the 1,3-bisacyloxy-2-methylenepropane is 1,3-diacetoxy-2-methylenepropane.

4. The production method according to claim 1, wherein an amount of the catalyst used is from 0.01 to 20% by mass based on the total mass of the carboxylic acid and the isobutylene.

5. The production method according to claim 1, wherein an amount of the catalyst activator used is from 1 to 20% by mass based on the total amount of the mass of the carrier and the amount of the catalyst activator used as 100% by mass, and wherein the catalyst activator is carried on the catalyst.

6. The production method according to claim 1, wherein a reaction temperature in the reaction in a liquid phase is from 80 to 200° C.

\* \* \* \* \*